US00PP21109P2

(12) United States Plant Patent
Tonies

(10) Patent No.: US PP21,109 P2
(45) Date of Patent: Jun. 29, 2010

(54) ***PHLOX* PLANT NAMED 'DITOMSUR'**

(50) Latin Name: *Phlox paniculata*
Varietal Denomination: Ditomsur

(75) Inventor: Hubertus Josephus Tonies, Noordwijkerhout (NL)

(73) Assignee: Kaster Beheer B.V., Boskoop (NL)

( * ) Notice: Subject to any disclaimer, the term of this patent is extended or adjusted under 35 U.S.C. 154(b) by 40 days.

(21) Appl. No.: 12/315,160

(22) Filed: Nov. 28, 2008

(51) Int. Cl.
*A01H 5/00* (2006.01)

(52) U.S. Cl. ..... Plt./320

(58) Field of Classification Search ..... Plt./320
See application file for complete search history.

(56) References Cited

OTHER PUBLICATIONS

UPOV ROM GTITM Computer Database, GTI Jouve Retrieval Software 2009/04 Citation for 'Ditomsur'.*

Bailey Nurseries Plant Summary *Phlox paniculata* 'Ditomsur' PPAF accessed Mar. 4, 2010 at http:// bailey.virtual-services.net/presslib/summary/6355/0.*

* cited by examiner

*Primary Examiner*—Wendy C. Haas
(74) *Attorney, Agent, or Firm*—C. A. Whealy

(57) ABSTRACT

A new and distinct cultivar of *Phlox* plant named 'Ditomsur', characterized by its compact and upright plant habit; strong stems; dark-colored stems and leaves; large red purple-colored flowers; and tolerance to Downy Mildew.

3 Drawing Sheets

Botanical designation: *Phlox paniculata.*
Cultivar denomination: 'DITOMSUR'.

BACKGROUND OF THE INVENTION

The present invention relates to a new and distinct cultivar of *Phlox* plant, botanically known as *Phlox paniculata* and hereinafter referred to by the name 'Ditomsur'.

The new *Phlox* plant is a product of a planned breeding program conducted by the Inventor in Noordwijkerhout, The Netherlands. The objective of the breeding program is to create new compact *Phlox* cultivars with attractive leaf and flower coloration and disease resistance.

The new *Phlox* plant originated from a cross-pollination in Noordwijkerhout, The Netherlands in July, 2000 of two unnamed seedling selections of *Phlox paniculata,* not patented. The new *Phlox* was discovered and selected by the Inventor as a single flowering plant from within the progeny of the stated cross-pollination in a controlled environment in Noordwijkerhout, The Netherlands in July, 2001.

Asexual reproduction of the new *Phlox* plant by cuttings in a controlled environment in Noordwijkerhout, The Netherlands since 2001, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Ditomsur'. These characteristics in combination distinguish 'Ditomsur' as a new and distinct cultivar of *Phlox:*

1. Compact and upright plant habit.
2. Strong stems.
3. Dark-colored stems and leaves.
4. Large red purple-colored flowers.
5. Tolerant to Downy Mildew.

Plants of the new *Phlox* differ primarily from plants of the female parent selection in the following characteristics:

1. Plants of the new *Phlox* have darker-colored leaves than plants of the female parent selection.
2. Plants of the new *Phlox* are more freely flowering than plants of the female parent selection.
3. Plants of the new *Phlox* are more tolerant to Downy Mildew than plants of the female parent selection.

Plants of the new *Phlox* differ primarily from plants of the male parent selection in the following characteristics:

1. Plants of the new *Phlox* are taller than plants of the male parent selection.
2. Plants of the new *Phlox* and the male parent selection differ in flower color as plants of the male parent selection have dark purple-colored flowers.
3. Plants of the new *Phlox* are more freely flowering than plants of the male parent selection.

Plants of the new *Phlox* can also be compared to plants of *Phlox paniculata* 'Laura', not patented. In side-by-side comparisons conducted in Noordwijkerhout, The Netherlands, plants of the new *Phlox* and 'Laura' differed primarily in the following characteristics:

1. Plants of the new *Phlox* had darker-colored foliage than plants of 'Laura'.
2. Flowers of plants of the new *Phlox* were darker in color than flowers of plants of 'Laura'.

3. Plants of the new *Phlox* were tolerant to Downy Mildew whereas plants of 'Laura' were less tolerant to Downy Mildew.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph on the first sheet comprises a side perspective view of a typical plant of 'Ditomsur' grown in a container.

The photograph on the second sheet is a close-up view of typical leaves of 'Ditomsur'.

The photograph on the third sheet is a close-up view of a typical inflorescence of 'Ditomsur'.

DETAILED BOTANICAL DESCRIPTION

The aforementioned photographs and following observations, measurements and values describe plants grown in Boskoop, The Netherlands, under commercial practice during the summer in containers in an outdoor nursery. During the production of the plants, day temperatures ranged from 12° C. to 30° C. and night temperatures ranged from 4° C. to 16° C. Plants had been growing for one year when the photographs and description were taken. In the following description, color references are made to The Royal Horticultural Society Colour Chart, 2001 Edition, except where general terms of ordinary dictionary significance are used.

Botanical Classification: *Phlox paniculata* 'Ditomsur'.

Parentage:

*Female, or seed, parent.*—Unnamed selection of *Phlox paniculata,* not patented.

*Male, or pollen, parent.*—Unnamed selection of *Phlox paniculata,* not patented.

Propagation:

*Type.*—By cuttings.

*Time to initiate roots.*—About two weeks at 15° C. to 25° C.

*Time to produce a rooted young plant.*—About 35 days at 15° C. to 25° C.

*Root description.*—Fibrous, thin; pale cream tan in color.

*Rooting habit.*—Moderate branching; dense.

Plant description:

*Plant form/habit.*—Compact and upright plant habit; moderately vigorous growth habit.

*Branching habit.*—Freely branching habit with about five lateral branches per plant; pinching enhances branching.

*Plant height.*—About 32.1 cm.

*Plant width* (*spread*).—About 33.4 cm.

*Lateral branches.*—Length: About 24.2 cm. Diameter: About 5 mm. Internode length: About 2.7 cm. Strength: Strong. Texture: Smooth, glabrous. Color: Close to 146B.

Foliage description:

*Arrangement.*—Opposite, simple.

*Length.*—About 11.2 cm.

*Width.*—About 4.6 cm.

*Shape.*—Narrowly ovate to elliptic.

*Apex.*—Narrowly acute.

*Base.*—Obtuse.

*Margin.*—Very finely serrate.

*Texture, upper and lower surfaces.*—Smooth, glabrous.

*Venation pattern.*—Pinnate.

*Color.*—Developing leaves, upper surface: Darker than 147A heavily flushed with close to N186A to N186B. Developing leaves, lower surface: Darker than 147A. Fully expanded leaves, upper surface: Close to 137A; venation, close to 145B to 145C. Fully expanded leaves, lower surface: Close to 137C; venation, close to 145B.

*Petioles.*—Length: About 2.5 mm. Diameter: About 3 mm. Texture, upper and lower surfaces: Smooth, glabrous. Color, upper and lower surfaces: Close to 144B.

Flower description:

*Flower type/habit.*—Single rotate flowers arranged in terminal compound panicles; flowers face mostly upright or outwardly. Panicles rounded and hemispherical in shape. Freely flowering habit with about 80 flowers developing per inflorescence.

*Fragrance.*—Moderately fragrant; sweet and pleasant.

*Natural flowering season.*—Continuously flowering from July to September in The Netherlands.

*Postproduction longevity.*—Flowers last about ten days on the plant; flowers not persistent.

*Flower buds.*—Height: About 1.3 cm. Diameter: About 4 mm. Shape: Narrowly oblanceolate. Color: Close to 70A; lower half, close to N186C; base, close to 145C to 145D.

*Inflorescence height.*—About 13 cm.

*Inflorescence diameter.*—About 10.8 cm.

*Flower diameter.*—About 3.3 cm.

*Flower depth.*—About 2.9 cm.

*Petals.*—Quantity per flower: Typically five in a single whorl; petals fused at the base into a narrow tube. Length from throat: About 1.6 cm. Length fused: About 1.6 cm. Lobe width: About 1.4 cm. Lobe shape: Roughly spatulate. Apex: Rounded. Margin: Entire. Texture, upper and lower surfaces: Smooth, glabrous. Color: Developing petals, upper surface: Close to N78A; spots, between 76D and N155A; towards the throat, close to N74A to N74B; throat, close to N77B. Developing petals, lower surface: Close to 77B; tube, close to N79B. Fully expanded petals, upper surface: Close to N78A; spots, between 76D and N155A; towards the throat, darker than N74A; throat, close to N77B. Fully expanded petals, lower surface: Close to 77B; tube, close to N79B.

*Sepals.*—Quantity per flower: Typically five in a single whorl, fused towards the base. Length: About 7 mm. Width: About 1.7 mm. Shape: Lanceolate. Apex: Narrowly apiculate. Margin: Entire. Texture, upper and lower surfaces: Smooth, glabrous. Color: Developing sepals, upper and lower surfaces: Close to N186C; towards the base, close to 145C to 145D. Fully expanded sepals, upper and lower surfaces: Close to N186C; towards the margins, close to 145C to 145D.

*Peduncles.*—Length: About 9.5 cm. Diameter: About 3 mm. Strength: Strong. Texture: Smooth, glabrous. Color: Close to 146B.

*Pedicels.*—Length: About 5 mm. Diameter: About 1 mm. Strength: Strong. Texture: Smooth, glabrous. Color: Close to 144C.

*Reproductive organs.*—Stamens: Quantity per flower: Typically five. Filament length: About 4 mm. Anther shape: Oblong. Anther length: About 2 mm. Anther color: Close to 8D. Pollen amount: Scarce to moderate. Pollen color: Close to 11D. Pistils: Quantity per flower: One. Pistil length: About 1.6 cm. Stigma shape: Three-parted. Stigma color: Close to 150D. Style length: About 1.5 cm. Style color: Close to N186C. Ovary color: Close to 143A.

*Seed/fruit.*—Seed and fruit development have not been observed.

Disease/pest resistance: Plants of the *Phlox* have been observed to be tolerant to Downy Mildew. Plants of the new *Phlox* have not been observed to be resistant to pests or other pathogens common to *Phlox*.

Garden performance: Plants of the new *Phlox* have been observed to have good garden performance and tolerate ram, wind and temperatures ranging from about −20° C. to about 40° C.

It is claimed:

1. A new and distinct *Phlox* plant named 'Ditomsur' as illustrated and described.

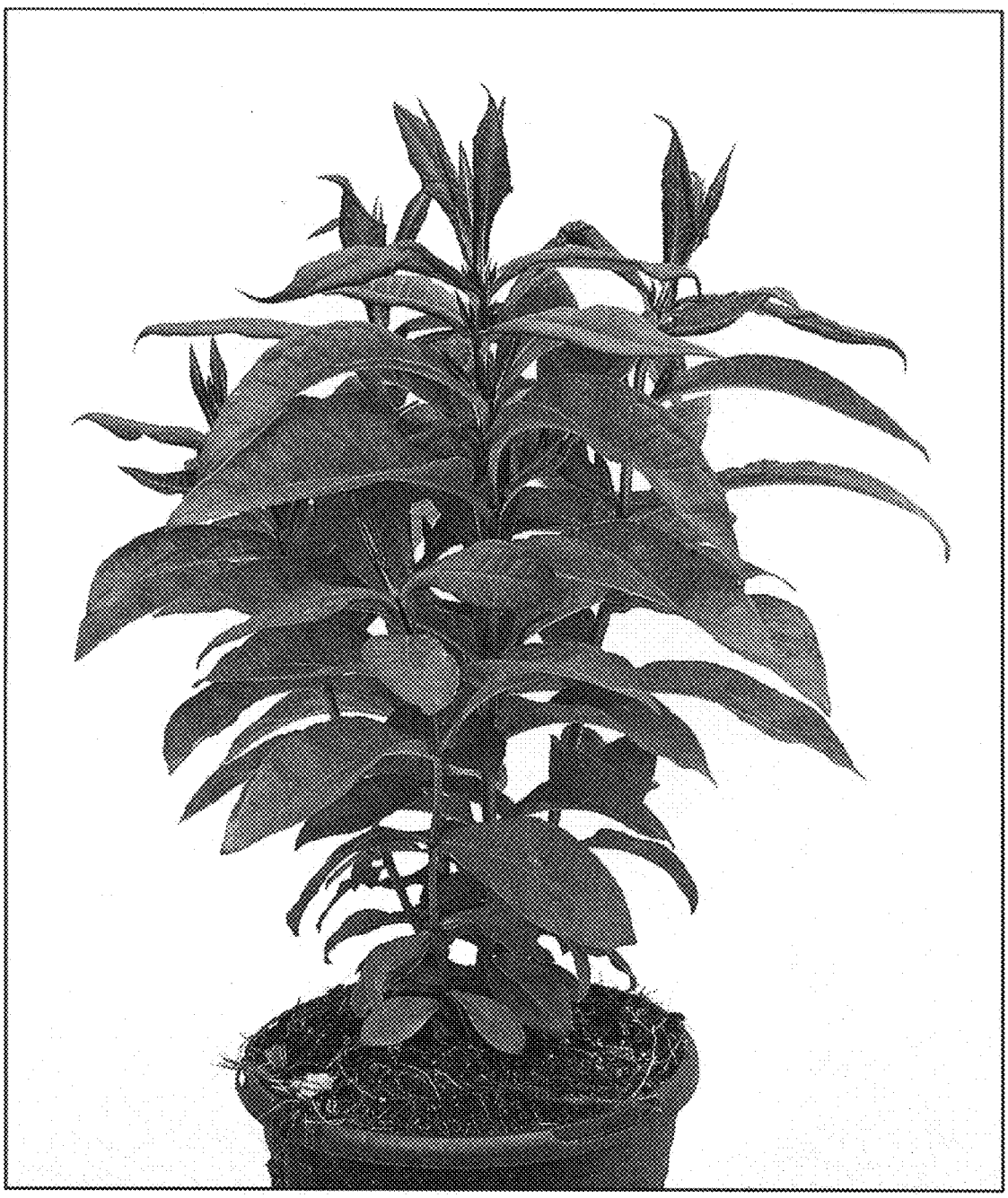

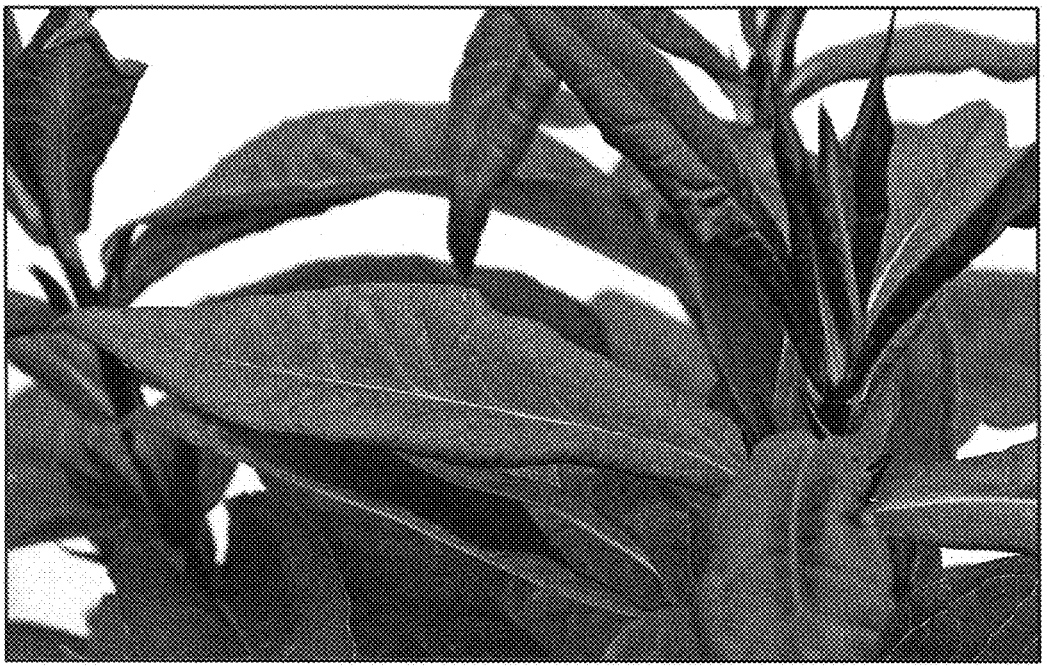

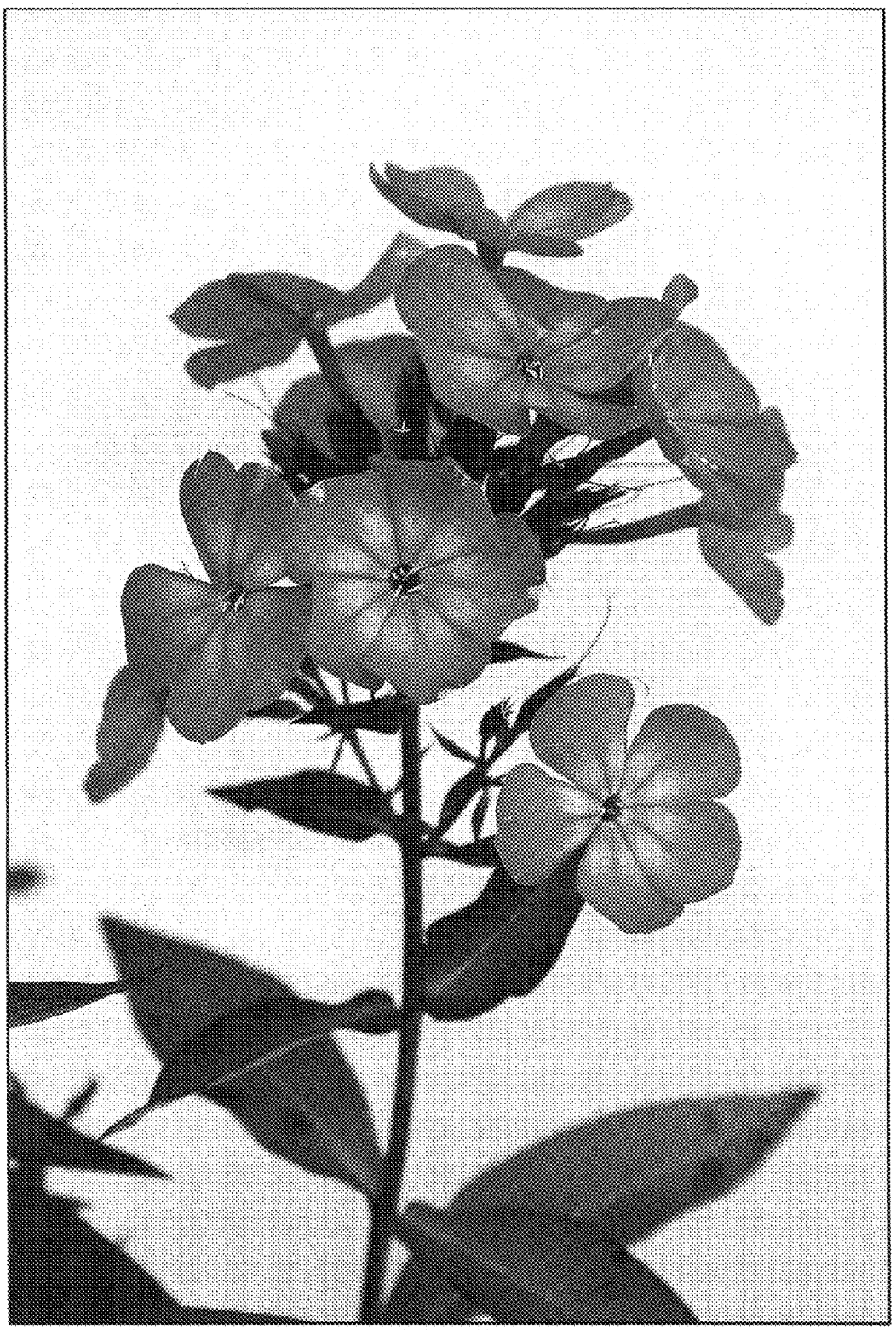

* * * * *